(12) United States Patent
Akkaya

(10) Patent No.: US 7,090,489 B2
(45) Date of Patent: Aug. 15, 2006

(54) MAXILLARY PROTRACTION DEVICE WITH CHIN-CUP

(76) Inventor: Sevil Akkaya, Kumkapi Sokak 35/6 G.O.P., Ankara 06110 (TR)

( * ) Notice: Subject to any disclaimer, the term of this patent is extended or adjusted under 35 U.S.C. 154(b) by 0 days.

(21) Appl. No.: 10/491,258

(22) PCT Filed: Sep. 27, 2002

(86) PCT No.: PCT/TR02/00059

§ 371 (c)(1),
(2), (4) Date: Mar. 30, 2004

(87) PCT Pub. No.: WO03/028578

PCT Pub. Date: Apr. 10, 2003

(65) Prior Publication Data

US 2004/0241605 A1    Dec. 2, 2004

(30) Foreign Application Priority Data

Oct. 1, 2001    (TR) .............................. a 2001 02776

(51) Int. Cl.
*A61C 3/00* (2006.01)
(52) U.S. Cl. .......................................................... 433/5
(58) Field of Classification Search ...................... 433/5
See application file for complete search history.

(56) References Cited

U.S. PATENT DOCUMENTS

| 3,401,457 | A | * | 9/1968 | Hickham | ......................... | 433/5 |
| 4,375,355 | A | * | 3/1983 | Dahan | ............................. | 433/5 |
| 4,375,962 | A | | 3/1983 | DeWoskin | ...................... | 433/5 |

FOREIGN PATENT DOCUMENTS

| FR | 2413076 | 7/1979 |
| WO | 97043975 | 11/1997 |

* cited by examiner

*Primary Examiner*—John J Wilson
(74) *Attorney, Agent, or Firm*—Adams & Wilks

(57) ABSTRACT

A maxillary protraction device (12) characterized with a chin-cup (1); one or more front hook-levers (2) on the front section of said chin-cup (1) to exert a force horizontally and forwards to the maxilla; at least two lateral linear hooks (5) located at the sides of the chin-cup (1) to exert an upwards force to the mandible, front recess (6) to be used for engaging the hooks (2 and 5) to the chin-cup (1) to which the front hook is engaged in a length-adjustable manner, in the same number as that of hooks; and fixing members (9) in the same number as that of hooks.

12 Claims, 2 Drawing Sheets

MAXILLARY PROTRACTION DEVICE WITH CHIN-CUP

CROSS REFERENCE TO RELATED APPLICATIONS

This application is a U.S. national stage application of International Application No. PCT/TR02/00059 filed Sep. 27, 2002, claiming a priority date of Oct. 1, 2001, and published in the English language.

BACKGROUND OF THE INVENTION

The present invention relates to a Modified Maxillary Protraction Device (MMPD) designed for the treatment of growing skeletal and dental open-bite cases accompanied by maxillary development deficiency.

Since a long time, the treatment of skeletal Class III malocclusions only by using orthodontical methods has been accepted to be difficult and subject to obstinancy. Before the 1970's, Class III problems were defined mainly as mandibular prognatisms, and maxilla has not been very much emphasized in the literature. Later studies have shown that a real isolated mandibular prognatism constitutes only 20–25% of Class III cases.

According to Sinclair and Proffit (Sinclair, P. M.; Proffit, W. R.: Class III Problems: Mandibular Excess/Maxillary Deficiency, in Surgical-Orthodontic Treatment. (ed.) Proffit, W. R.; White, R. P. St. Louis: Mosby, 1991, CH. 14, p: 428–482.) among the Class III anomalies, 20–25% of the Class III population exhibited only maxillary deficiency, whereas 50–60% exhibited maxillary deficiency, together with mandibular prognatism. This rate increases up to 32–43% in the Japanese society wherein the incidence of Class III anomalies is quite high (Takada, K.; Petdachai, S.; Sakuda, M.; Changes in Dentofacial Morphology in Skeletal Class III Children Treated by a Modified Maxillary Protraction Headgear and a Chincup: A Longitudinal Cephalometric Appraisal, Eur. J. Orthod. 15:211–221,1993.).

Excessive vertical development of the mandible, as well as its excessive forwards development, is quite common in Class III abnormality groups and constitutes a combination that can be seen in 6% of the patients.

The treatment plan for a skeletal Class III open-bite patient, during his/her growth period, should be aimed at both saggital and vertical anomalies, and excessive vertical growth of the mandible must be prevented while the forwards-downwards growth of the maxilla is encouraged.

In the devices used in the state of the art, the forwards development of the maxilla is provided and the forwards development of the mandible is inhibited. However, with the usage of maxillary protraction appliances, as the downwards growth of the mandible is not prevented, the length of the face increases. This situation may lead to the 'long-face syndrome' wherein chin-face (craniofacial) surgical operations may be required in skeletodental open-bite cases. For such a surgical intervention, the patient has to wait until he/she is 18 years old or a multi-phase orthodontic treatment that may last for many years with separate applications for the maxilla and mandible, has to be employed. During the multiphase orthodontical treatment, first a reverse head gear is implemented in order to increase the forwards maxillar development, however, the vertical open-bite status cannot be controlled by this implementation. Therefore the open-bite treatment is postponed to a later phase and requires the use of a separate apparatus.

Some orthodontists deem it convenient to wait until the completion of the growth of the Class III open-bite patients, without any interventions and upon the completion of their growth, to employ surgical methods to correct such anomalies. In the state of the art, in EU Patent No. 445492, the mandible is connected to magnets fastened by means of correcting levers to a control box. However here, only a vertical force is exerted on the chin.

In Spanish Patent Application No. 97/43975, a similar device is disclosed, whereby only a force in the vertical direction is applied on the chin by using correcting elements. Furthermore, the correcting elements have no length adjustment and movement possibilities.

In both of these prior art devices, conformity to all types of patient faces cannot be provided.

SUMMARY OF THE INVENTION

One object of the present invention is to prevent excessive vertical growth of the mandible and to provide an enhanced and rapid forward growth of the maxilla, without causing facial elongation in the growing individuals with Class III open-bite anomalies.

Another object of the present invention is to provide a simultaneous exertion of a horizontal-forwards force and a vertical-upwards force.

One other object of the present invention is to be able to terminate the exertion of the horizontal-forward force by removing the hooks when a sufficient relationship in forwards-backwards direction, between the mandible and the maxilla, is established.

Yet another object of the present invention is to be able to adjust the device in line with the facial structure of the individual.

Another object of the present invention is to realize the treatment in a short time, without subjecting a growing individual with many tiring procedures.

BRIEF DESCRIPTION OF THE DRAWINGS

The maxillary protraction device realized in order to attain the objects of the present invention has been illustrated in the drawings wherein.

DETAILED DESCRIPTION OF THE INVENTION

Figure 1:
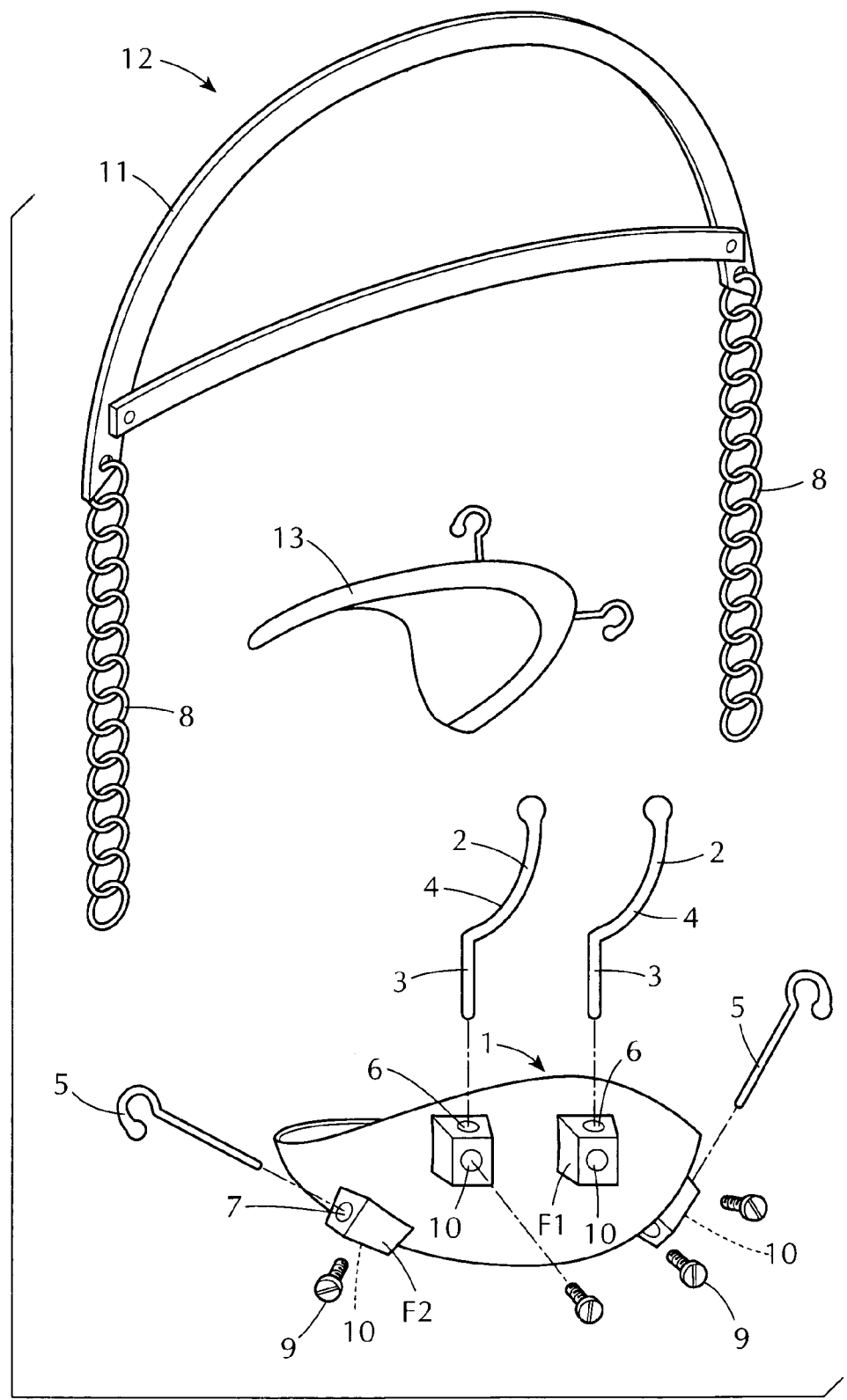
FIG. 1 is an exploded perspective view of a maxillary protraction device according to the present invention.

The maxillary protraction device (12) comprises a chin-cup (1); one or more front hooks or hook members (2) on the front section of the chin-cup (1) to exert a force horizontally and forwards to the chin; at least two lateral linear hooks or side hook members (5) located at the opposite sides of the chin-cup (1) to exert an upwards force to the chin orthogonally; a stationary or movable anchor act unit (13) placed on the upper palate; a head-piece (11) to be placed on the head; front openings (6) and lateral openings (7) for engaging the hooks (2 and 5) to the chin-cup (1), in the same number as that of the hooks; and fixing or locking members such as screws (9) in the same number as that of the hooks.

The head-piece (11) can be made in various shapes provided that it tightly fits onto the head. At the ear level, the head-piece is provided with flexible fastening members (8) to be connected to the lateral hooks (5) in order to exert an upwards force to the mandible.

The chin-cup (1) has a structure in conformity with the patients' chin structure. The openings (6 and 7) are adapted to slidably receive the hooks (2 and 5) and are provided with a fixing member hole such as a screw hole (10) in order to releasably fix the inserted hooks (2,5) in the openings (6,7).

Each front hook (2) consists of a linear-section (3) and a curved-section (4). The linear section (3) is slidably adjusted to the desired up-down position in the front opening (6) and is fixed by means of the fixing or locking member (9).

Each lateral hook (5) with a lateral-linear form is slidably adjusted to the desired front-rear position in the side or lateral opening (7) and is fixed by means of the fixing or locking member (9).

Figure 3:
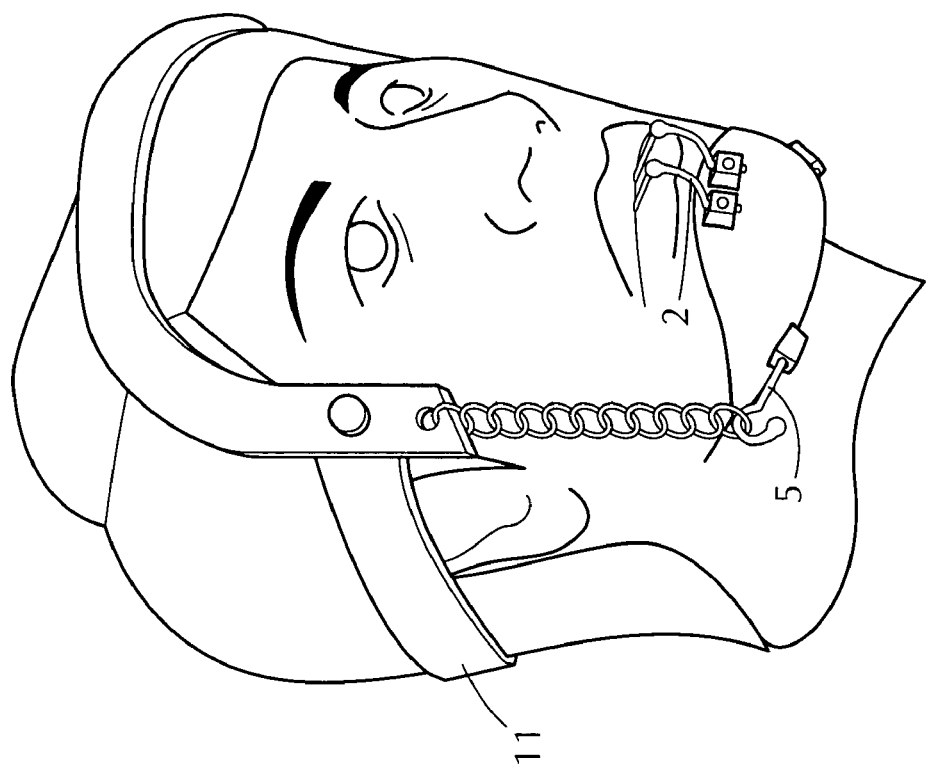
FIG. 3 is an exploded perspective view of the maxillary protraction device.
Figure 2:
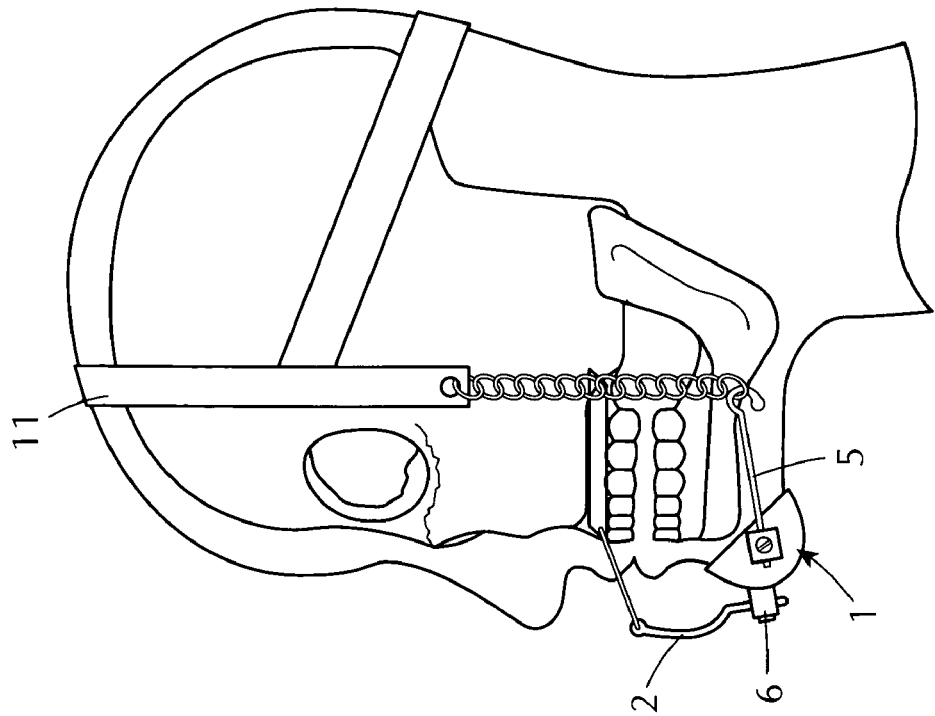
FIG. 2 is a profile view of the maxillary protraction device.

The front and lateral hooks (2 and 5) are preferably made of metal. The front openings (6) and the lateral openings (7) are formed in front and side fixtures F1 and F2 in the form of protrusions on the chin-cup (1). The front opening (6) has a length at least equal to the linear section (3) of the front hook (2) whereas the lateral opening (7) is at least as long as the lateral-linear hook (5). The front openings (6) extend completely through the front fixtures F1 in a generally up-down direction during use of the device (see FIGS. 2 and 3), and the lateral openings (7) extend completely through the side fixtures F2 in a generally front-rear direction during use of the device (12). The hooks (2 and 5) enter the openings from one end and project from the other end.

The chin-cup (1) is connected to the head-piece (11) by means of the lateral hooks (5), and a rubber piece that will exert a force of 400–450 gf is provided between the head-piece and the lateral hooks. The free ends of the lateral hooks (5) are adjustably positioned in the lateral openings (7) of the chin-cup, according to the facial dimensions of the patient, and fixed by means of the fixing member (9). The removable or fixed anchorage unit (13) is placed to the upper palate. The front hooks (2) are attached to the front openings (6) after being adjusted according to the facial structure of the patient and fixed by means of the fixing member (9).

The fastening members (8) are made of a flexible material such as rubber, and are placed between the front hooks (2) and the anchorage unit (13) within the mouth, on both sides, i.e., at left and right, in such a manner that they will each exert a force of 350 gf.

The treatment is continued until an adequate vertical and horizontal closure between the upper and lower incisors is obtained. When an adequate closing in the horizontal direction is obtained, the front hooks (2) are removed but as the vertical growth and development take more time, the lateral hooks (5) are used for a longer time. The device can be adapted to a smaller size by removing the unused hooks (2,5) from the chin-cup (1).

In another embodiment of the present invention, the lateral hooks are permanently fixed on the chin-cup.

With this invention, in the skeletal and dental open-bite cases accompanied by maxillary development deficiency in growing individuals, the maxillary forward development is obtained and the sagging of the mandible downwards due to excessive growth of the mandible in the vertical direction is inhibited. The device according to the present invention is easy to manufacture and has a low cost of production.

The invention claimed is:

1. A maxillary protraction device for correcting open-bite anomalies accompanied by maxillary deficiency, comprising: a chin-cup; one or more front hooks on the front section of the chin-cup to exert a force horizontally and forwards to the maxilla; at least two lateral linear hooks located at the sides of the chin-cup to exert a vertical upward force to the mandible; means on the chin-cup defining front and lateral openings each receiving therein one of the hooks, the one or more front hooks and the lateral hooks each being lengthwise adjustable in its corresponding opening; and fixing members releasably fixing respective ones of the hooks in respective ones of the openings.

2. A maxillary protraction device according to claim 1; wherein each front hook is removable from its corresponding opening.

3. A maxillary protraction device according to claim 1; wherein the lateral hooks are removable from their corresponding openings.

4. A maxillary protraction device according to claim 1; wherein each front hook has a linear lower section slidably inserted into one of the openings and a curved upper section for connection to an anchorage unit.

5. A maxillary protraction device according to claim 1; further including elastic fastening members each having one end connected to a head-piece and another end connected to one of the lateral hooks for exerting a vertical upward force on the mandible.

6. A maxillary protraction device according to claim 1; wherein the openings have a depth which is at least equal to the length of a linear section of the hooks.

7. A maxillary protraction device according to claim 1; wherein the fixing members comprise screws removably screwed into screw holes that open into respective ones of the openings for releasably fixing the hooks in the openings.

8. A maxillary protraction device for correcting open-bite anomalies accompanied by maxillary deficiency, comprising: a chin-cup configured to fit over the chin of a person using the device; one or more front fixtures disposed at a front portion of the chin-cup, each front fixture having an opening therethrough that extends in a generally up-down direction during use of the device; two side fixtures disposed at opposite sides of the chin-cup, each side fixture having an opening therethrough that extends in a generally front-rear direction during use of the device; a front hook member adjustably slideably inserted in the opening of each front fixture and releasably fixed in a desired up-down position in the opening by the front fixture; and a side hook member adjustably slideably inserted in the opening of each side fixture and releasably fixed in a desired front-rear position in the opening by the side fixture.

9. A maxillary protraction device according to claim 8; wherein the front and side fixtures each have a hole therein extending from a periphery thereof to the opening, and a locking member extending into the hole and releasably engaging with the hook member to releasably fix the hook member in the desired position.

10. A maxillary protraction device according to claim 9; wherein the holes in the fixtures are screw holes and the locking members are screws screwed into the screw holes.

11. A maxillary protraction device according to claim 8; further including elastic members each having one end connected to one of the side hook members and another end connected to a head-piece wearable by the person using the device.

12. A maxillary protraction device according to claim 8; further including an anchorage unit wearable in the mouth of the person using the device and connected to each front hook member.

* * * * *